United States Patent
Rutledge

(10) Patent No.: US 8,998,922 B2
(45) Date of Patent: Apr. 7, 2015

(54) LOCKING CAP RELEASE MECHANISM

(71) Applicant: Synthes USA, LLC, West Chester, PA (US)

(72) Inventor: Henry Rutledge, Audubon, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 182 days.

(21) Appl. No.: 13/679,004

(22) Filed: Nov. 16, 2012

(65) Prior Publication Data

US 2014/0142585 A1    May 22, 2014

(51) Int. Cl.
*A61B 17/58* (2006.01)
*A61B 17/60* (2006.01)
*A61F 2/00* (2006.01)
*A61B 17/70* (2006.01)

(52) U.S. Cl.
CPC ......... *A61B 17/7032* (2013.01); *A61B 17/7091* (2013.01); *A61B 17/7035* (2013.01)

(58) Field of Classification Search
USPC .......................................... 606/104
See application file for complete search history.

(56) References Cited

U.S. PATENT DOCUMENTS

| | | | |
|---|---|---|---|
| 8,221,472 | B2 | 7/2012 | Peterson et al. |
| 2006/0074418 | A1* | 4/2006 | Jackson .................. 606/61 |
| 2011/0160779 | A1 | 6/2011 | Schlaepfer et al. |
| 2011/0263945 | A1 | 10/2011 | Peterson et al. |

* cited by examiner

*Primary Examiner* — Andrew Yang
(74) *Attorney, Agent, or Firm* — Meunier Carlin & Curfman, LLC

(57) ABSTRACT

The present invention is directed to a release mechanism for removing and/or releasing a locking cap from the head of a bone anchor in situ. The release mechanism includes a sleeve, an anchor coupling member and a knob. The anchor coupling member is located within the sleeve and the knob engages both the anchor coupling member and the sleeve. The distal end of the sleeve and anchor coupling member engage the bone anchor causing the bone anchor to splay from the locking cap. A driver may be inserted into the central bore of the release mechanism to release any further threaded engagement of the locking cap and the bone anchor.

20 Claims, 8 Drawing Sheets

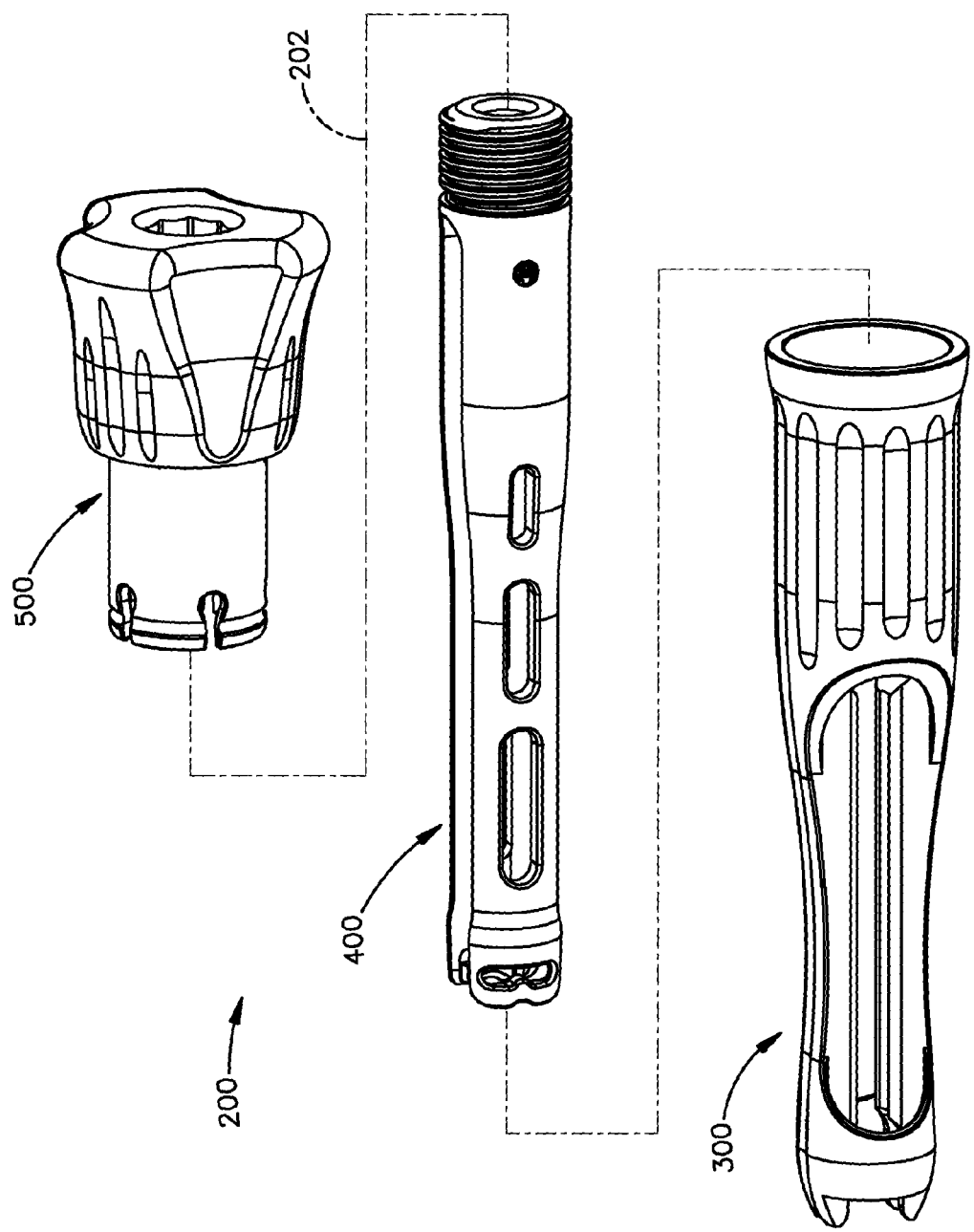

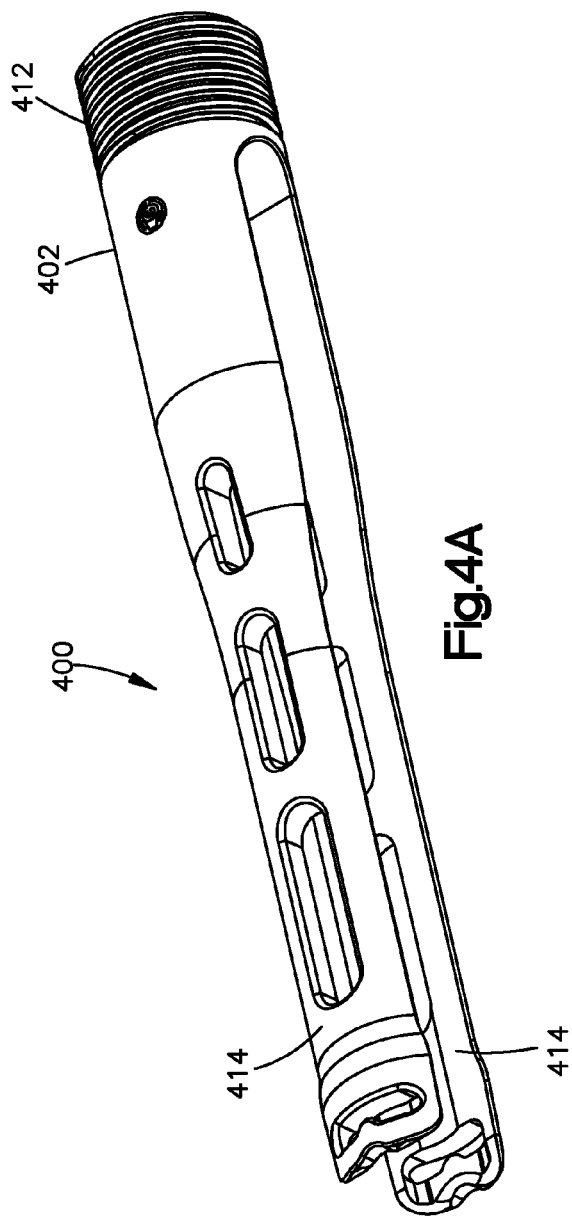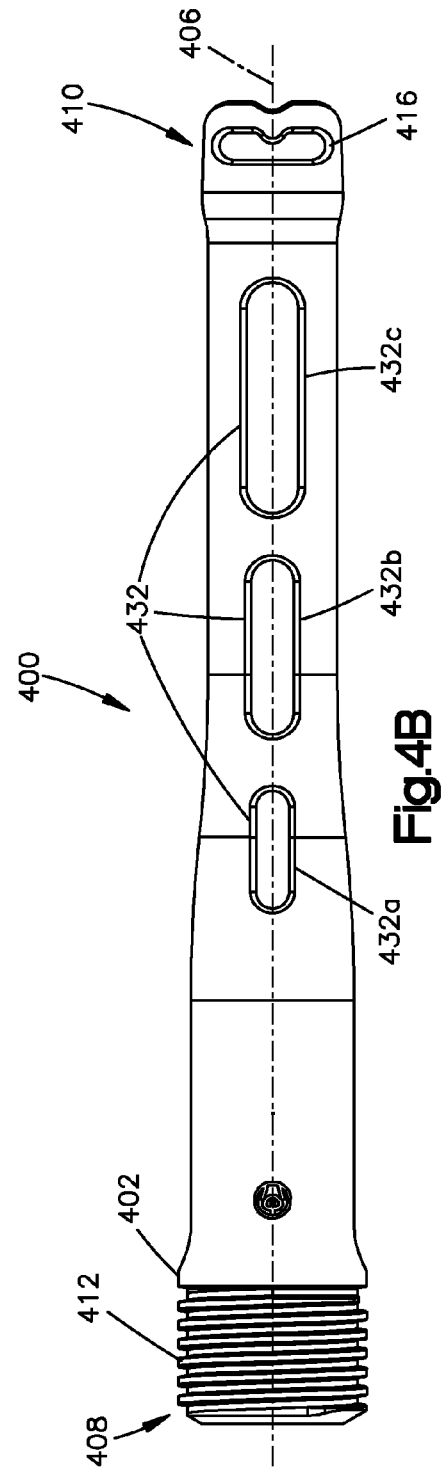

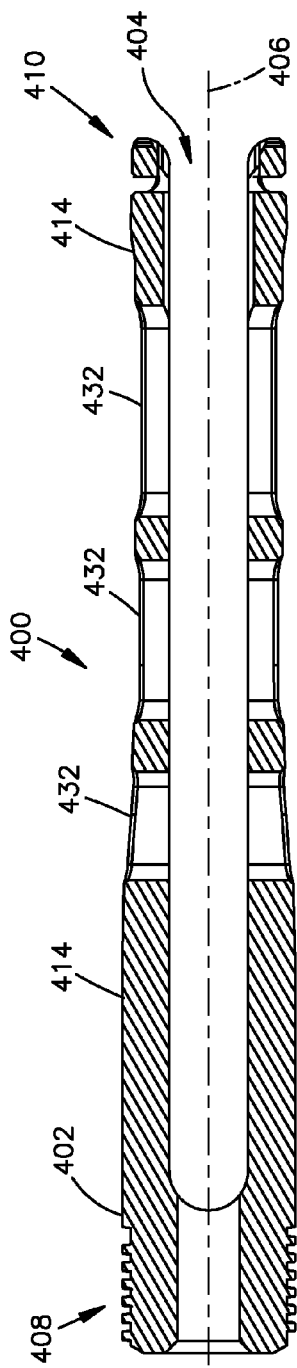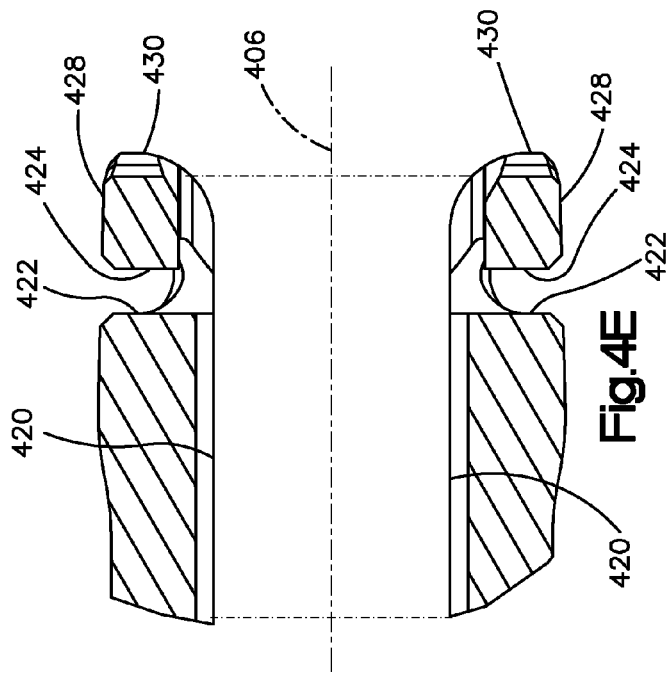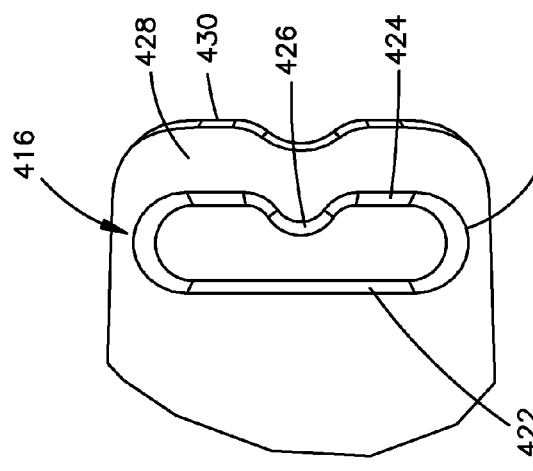

LOCKING CAP RELEASE MECHANISM

TECHNICAL FIELD

This invention generally relates to a device for loosening a locking cap from a bone anchor head. More specifically, the invention relates to a device for splaying the threads of the bone anchor head from the threads of the locking cap in situ.

BACKGROUND

One method of treating spinal disorders involves anchoring a screw or a hook to a patient's vertebrae. The screws or hooks are fixed along a spinal rod to position or immobilize the vertebrae with respect to one another. The screws or hooks commonly have heads with channels in which the spinal rod is inserted and subsequently clamped in place by a set screw, fastener, or locking cap. The spinal rod may be shaped to maintain the vertebrae in an orientation to correct the spinal disorder (e.g., to straighten a spine having abnormal curvature). Additionally or alternatively, the screws or hooks may be spaced along the rods to compress or distract adjacent vertebrae.

It is not uncommon for the spinal rod to require adjustment and/or removal during the course of treatment. Adjustment or removal of the spinal rod requires the locking cap be removed or loosened from the bone screw head. Unfortunately, surgeons often encounter considerable difficulty when removing or adjusting a locking cap due to sticking or "locking" of the cap within the bone screw. Because the bone screw and locking cap are subjected to prolonged immersion in bodily fluids, the threads of these components can become "locked" together due to the shear-thinning properties of blood coupled with blood's natural congealing process when exposed to air. The threads can also become locked together due to the cold welding effect of the thread surfaces of the locking cap and the screw head.

One current method of addressing the thread locking of the screw head and locking cap include the cyclic application of a tightening and loosening torque using a torque-limiting handle. This, and other methods for "unlocking" a locking cap, frequently result in the application of a torque in excess of the locking cap's design limits causing fracture of the locking cap and the potential for non-implantable grade stainless steel to become buried within the bone screw/implant. Therefore, a need exists for a device that provides for the removal of a "locked" locking cap thereby reducing procedure completion time and risk to the patient.

SUMMARY

Presented are systems and methods for removing and/or releasing a locking cap from the head of a bone anchor. An aspect of the present disclosure is directed to a release mechanism for releasing a locking cap threadingly engaged with a bone anchor. The release mechanism may include a sleeve, an anchor coupling member and a knob. The sleeve may comprise a sleeve bore extending along a longitudinal axis of the sleeve. The distal end of the sleeve may be sized and configured to surround at least a portion of the locking cap and the bone anchor head. The distal end of the sleeve may include a saddle portion configured to abut a rod retained between the locking cap and the bone anchor head when assembled. The anchor coupling member may include a body portion having a proximal end that releasably mates with a knob. The body portion may include an inner bore extending along the longitudinal axis of the anchor coupling member. The anchor coupling member may further include an arm extending from the body portion. The arm may be sized and configured to cover at least a portion of the locking cap and the bone anchor head and may include a coupling feature at a distal end sized and configured to matingly engage a corresponding coupling feature of the bone anchor head. The knob may include a handle, a knob body, and a knob bore extending through the handle and knob body along a longitudinal axis of the knob. The knob bore may include a mating portion for releasably mating the knob with the anchor coupling member. Further, the sleeve bore may be sized and configured to receive at least a portion of the anchor coupling member and a portion of the knob body.

Another aspect of the present disclosure is directed to a method of releasing a locking cap attached to a bone anchor. The method may include assembling a release mechanism by inserting a portion of an anchor coupling member into a bore in a release sleeve and aligning a side of a sleeve saddle portion with a side of a coupling feature of an anchor coupling member. The sleeve saddle portion may extend from a distal end of the release sleeve and the coupling feature may extend from a distal end of the anchor coupling member.

Assembling the release mechanism may further include attaching a knob to the anchor coupling member by inserting a portion of the knob into the release sleeve such that an inner bore of the knob matingly engages with the anchor coupling member. The method may further include attaching the coupling feature to a corresponding coupling feature on the bone anchor such that the sleeve saddle portion impacts a rod retained between the locking cap and the bone anchor and the coupling feature splays a side of the bone anchor from the locking cap.

The details of one or more embodiments of the invention are set forth in the accompanying drawings and the description below. Other features, objects, and advantages of the invention will be apparent from the description and drawings, and from the claims.

DESCRIPTION OF DRAWINGS

The device is explained in even greater detail in the following exemplary drawings. The drawings are merely exemplary to illustrate the structure of preferred devices and certain features that may be used singularly or in combination with other features. The invention should not be limited to the embodiments shown.

FIG. 2A is an exploded perspective view of an exemplary release mechanism;

FIG. 4A is a perspective view of an exemplary anchor coupling;

FIG. 4B is a top view of an exemplary anchor coupling;

FIG. 4C is a side cross-section view of an exemplary anchor coupling;

FIG. 4D is a detail view of an exemplary anchor coupling;

FIG. 4E is a detail view of an exemplary anchor coupling;

DETAILED DESCRIPTION

Figure 1:
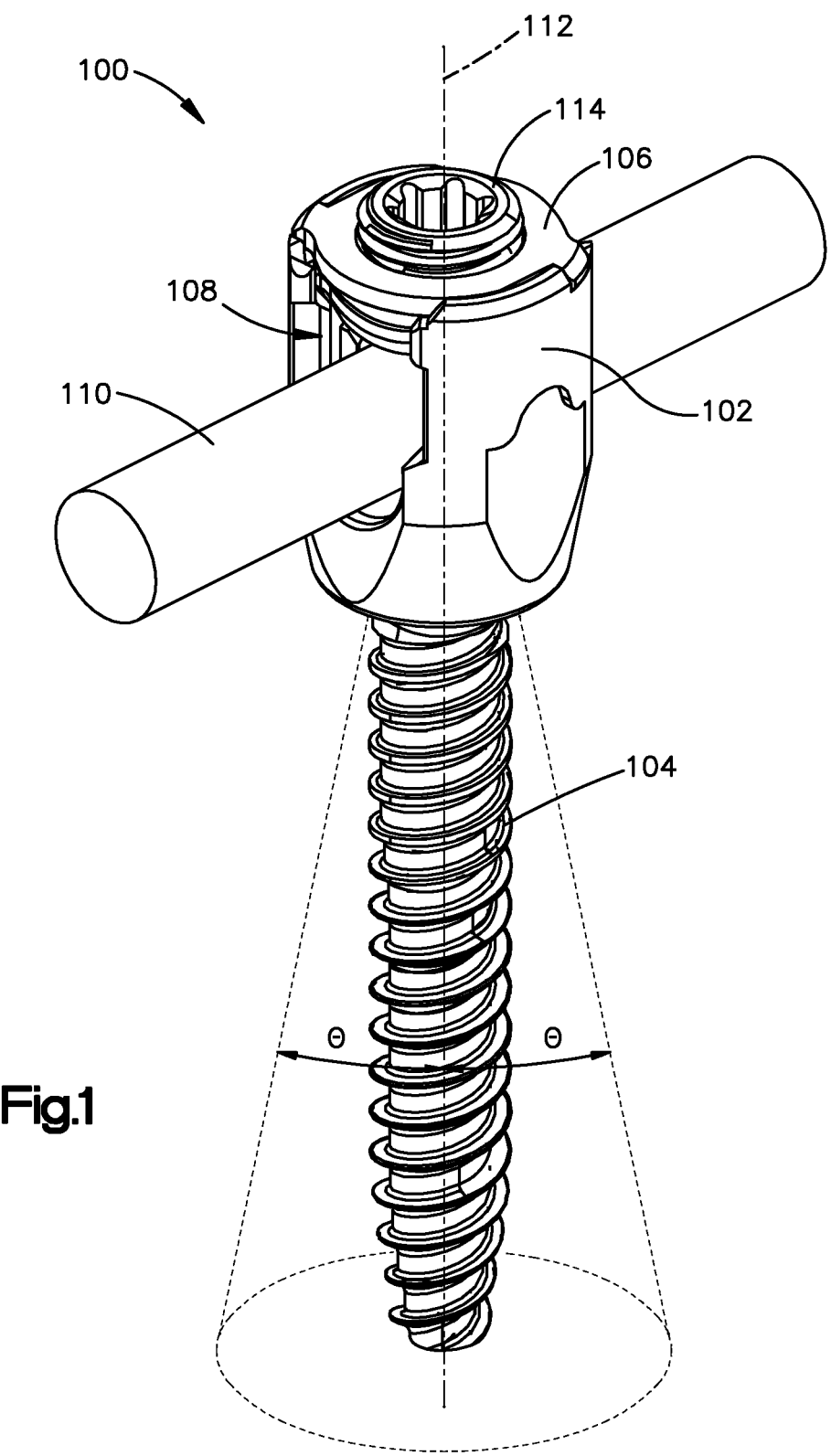
FIG. 1 is a perspective view of an exemplary polyaxial bone anchor.

Certain exemplary embodiments of the invention will now be described with reference to the drawings. In general, such embodiments relate to a device for loosening a locking cap from a bone anchor head in situ. FIG. 1 is a perspective view of an exemplary polyaxial bone anchor assembly 100, polyaxial bone screw or polyaxial pedicle screw.

The exemplary polyaxial bone anchor 100 includes an anchor head 102, a threaded anchor member 104 and a locking cap 106. The bone anchor 100 may also be a monoaxial bone anchor such that the anchor member and anchor head are integral members that are fixed together (not shown). The threaded anchor member 104 includes a plurality of threads for securing the bone anchor 100 to a vertebra, bone segment, or other tissue of a patient.

The anchor head 102 has a generally U-shaped opening or channel 108 for receiving a spinal rod 110 or other device, such as, for example, a plate. The threaded anchor member 104, which may be a bone screw, hook, reduction screw, sagittal screw, and iliac connector, or other similar structure, is coupled to anchor head 102 such that is rotatable and pivotable with respect to the anchor head 102. In an exemplary embodiment, the threaded anchor member 104 can angularly rotate about axis 112. It is contemplated that one or more bone anchors 100 may be attached to the vertebrae via respective anchor members 104, a spinal rod 110 or other device can be inserted into the U-shaped openings 108 and thereafter locked into position to aid in aligning the spine or treat other spinal disorders.

FIG. 1 shows locking cap 106 locked into anchor head 102. Locking cap 106 generally includes a main body and a saddle portion that abuts the spinal rod 110 inserted into the U-shaped openings 108 of the anchor head 102. In an exemplary embodiment, the main body of the locking cap 106 includes an external threaded portion that mates with a corresponding internal threaded portion of the anchor head 102. In a particular embodiment, the locking cap 106 may include a star-shaped socket and a locking screw 114 located on the top of the locking cap 106 body for mating with associated drivers. In an alternative embodiment, the locking cap 106 may include any other types of sockets or recesses keyed to other known drivers or tools. A predetermined torque may be applied to the locking cap 106 and/or locking screw 114 to fix the locking cap 106 in position when the rod is located in a treatment position. To remove and/or release the locking cap 106 from the anchor head 102 a release mechanism 200 may be used.

As illustrated in FIG. 2A, the release mechanism 200 may include, for example, a sleeve 300, an anchor coupling member 400 and a knob 500. The release mechanism 200 may be configured such that the sleeve 300, anchor coupling member 400 and the knob 500 work together to splay the anchor head 102 from the locking cap 106. In an exemplary embodiment, the release mechanism 200 can be used to separate or pull apart the threads of the anchor head 102 from the threads of the locking cap 106. The release mechanism 200 may include a central opening or bore that continues along the longitudinal axis 202 of the device through the sleeve 300, anchor coupling member 400 and the knob 500. In an exemplary embodiment, a driver or other tool may be inserted through the central opening in the release mechanism 200 to manipulate the anchor 100. For example, a screwdriver may be inserted into the central opening of the release mechanism 200 to loosen and/or remove the locking cap 106 from the anchor head 102 either before, after or while the threads of the anchor head 102 are splayed from the threads of the locking cap 106.

Figure 2B:
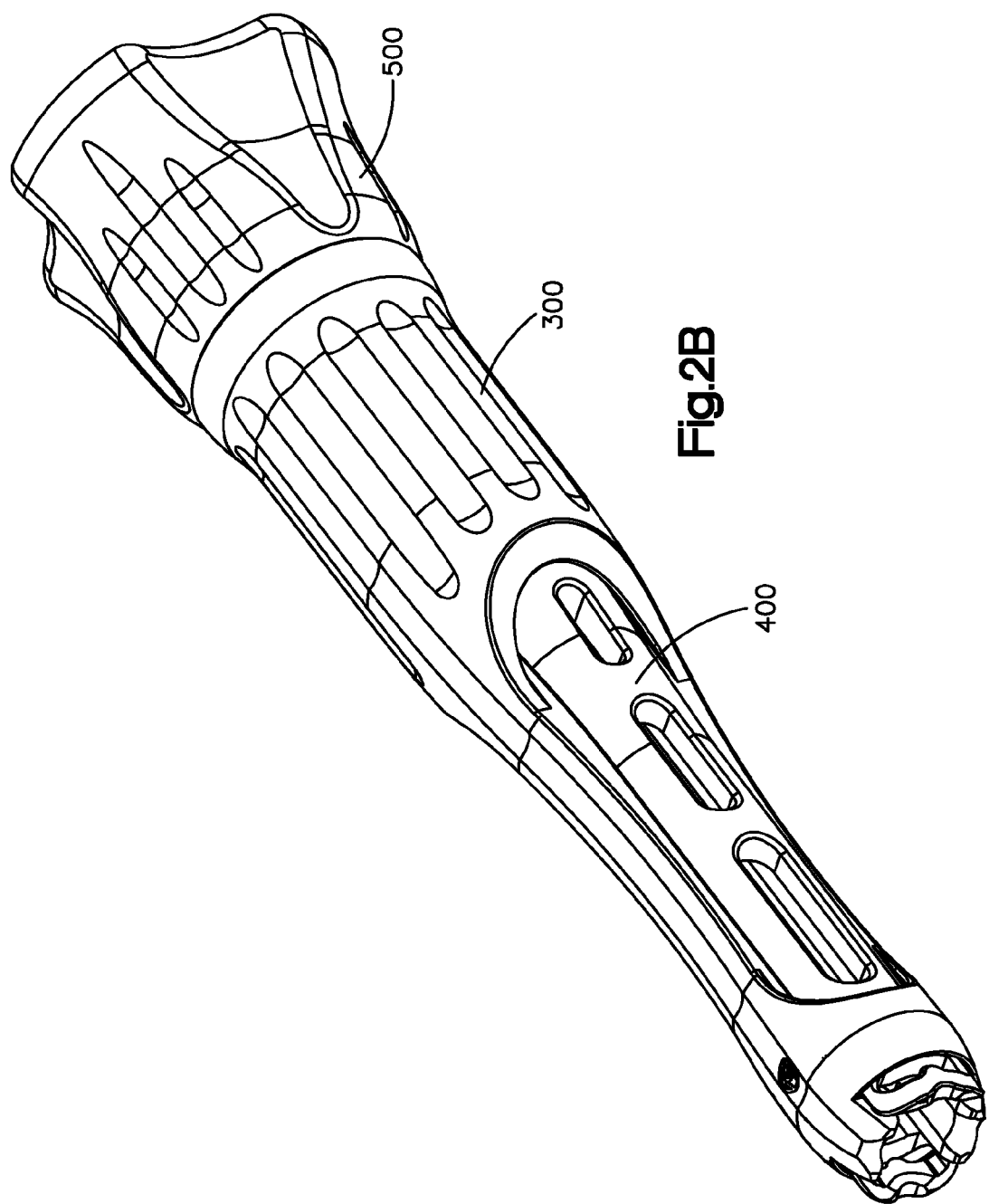
FIG. 2B is a perspective view of an exemplary release mechanism.

As shown in FIG. 2B, and explained in more detail below, when assembled the anchor coupling member 400 can be positioned within the sleeve 300. It is contemplated that the knob 500 can engage the proximal ends of the anchor coupling member 400 and/or sleeve 300 before or after the anchor coupling member 400 is inserted into the sleeve 300. In an exemplary embodiment, when assembled the knob 500 engages both the anchor coupling member 400 and the sleeve 300.

Figure 3A:
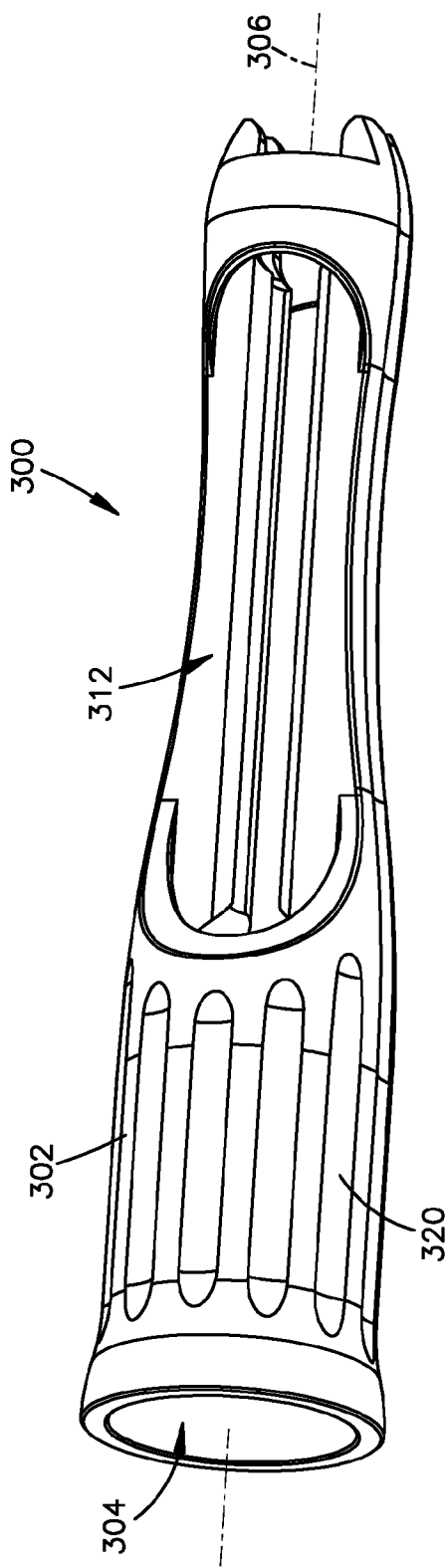
FIG. 3A is a perspective view of an exemplary sleeve.
Figure 3B:
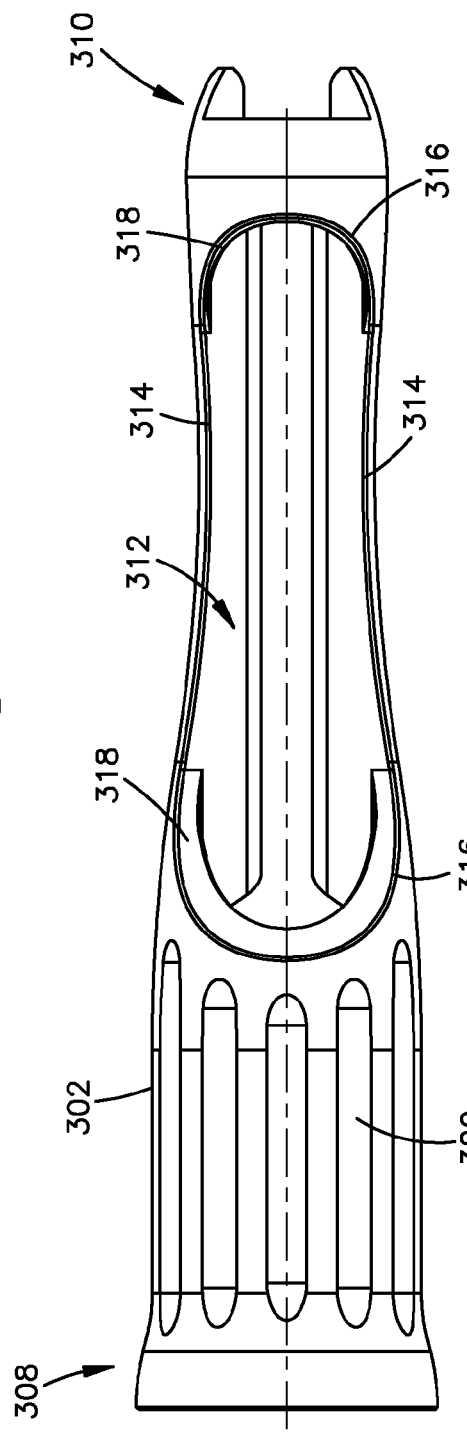
FIG. 3B is a top view of an exemplary sleeve.
Figure 3C:
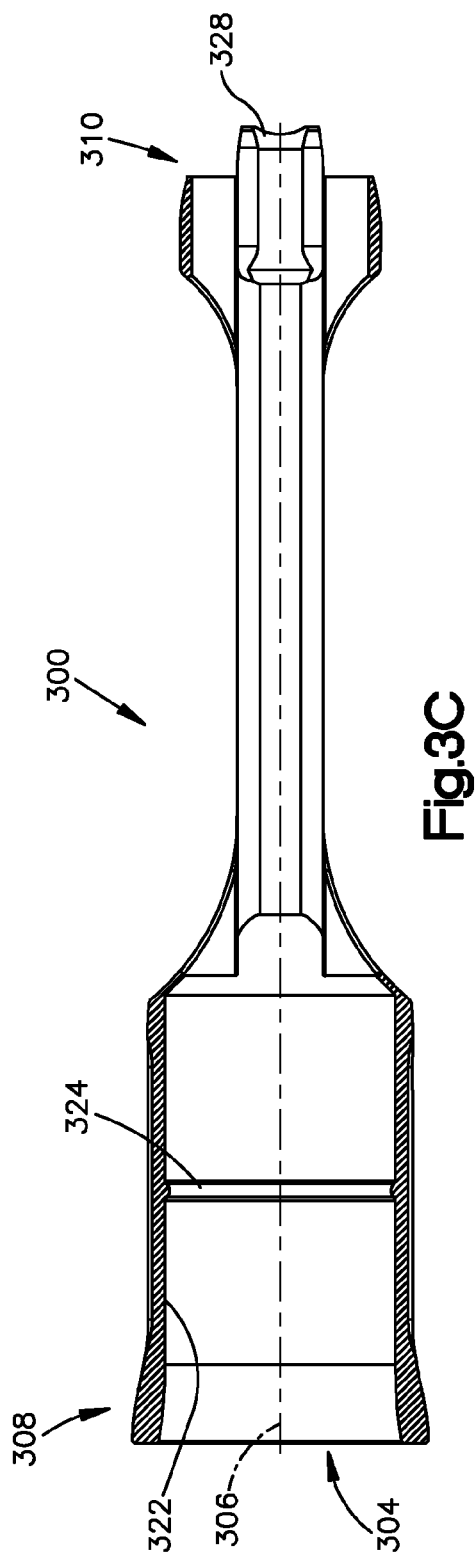
FIG. 3C is a side cross-section view of an exemplary sleeve.
Figure 3D:
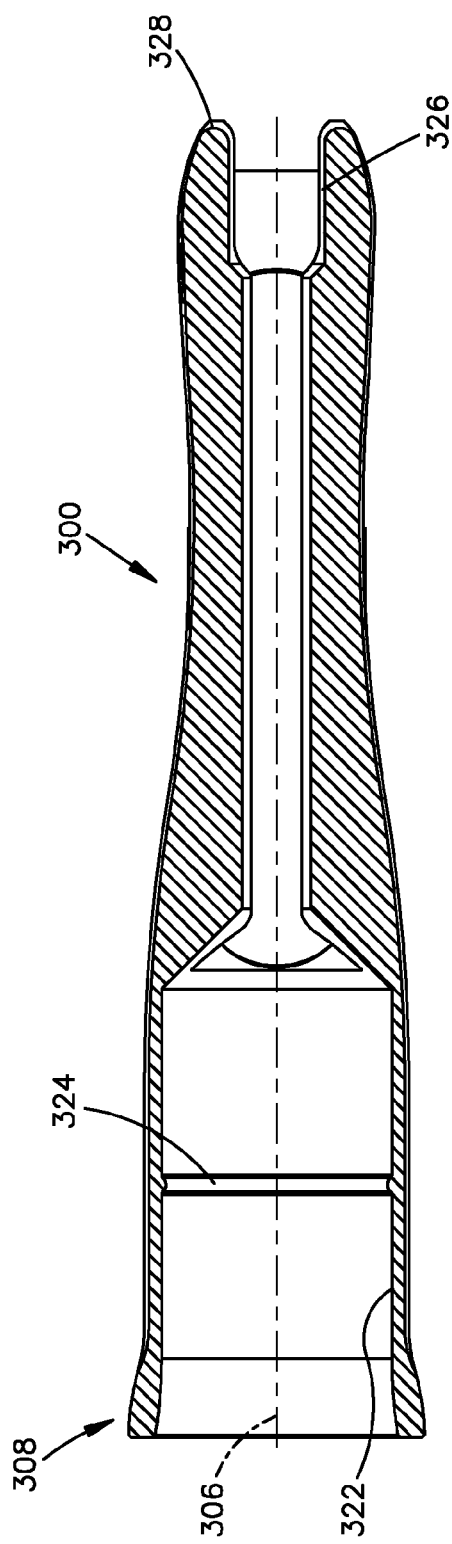
FIG. 3D is a top cross-section view of an exemplary sleeve.

FIGS. 3A-D provide multiple views of the sleeve 300 according to exemplary embodiments of the present disclosure. The sleeve 300 may include a generally cylindrical body 302 with a central bore 304 extending along the longitudinal axis 306 of the sleeve 300. In an exemplary embodiment, as illustrated in FIGS. 3B and 3D, the outer surface of the body 302 defines a curvilinear profile that tapers from the proximal end 308 to the distal end 310 of the sleeve 300. In an alternate embodiment (not shown), the outer surface of the body 302 defines a profile that maintains a constant dimension along the longitudinal axis 306. In a further embodiment (not shown), the outer surface of the body 302 defines a curvilinear profile that tapers from the distal end 310 to the proximal end 308.

In an exemplary embodiment, the sleeve body 302 may include an opening 312. The opening 312 can provide visibility to the interior of the sleeve 300 as well as visibility of the anchor coupling member 400 inserted into the sleeve 300 during assembly. It is also contemplated that the opening 312 will make the sleeve 300 lighter, reduce manufacturing and material costs, and expedite cleaning and sterilization of the sleeve 300. The sleeve 300 may include a single opening 312 or multiple openings 312 spaced apart around the body 302. In an exemplary embodiment, the sleeve 300 includes two openings 312 spaced equidistant from each on opposite sides of the sleeve body 302. The perimeter of the opening 312 can define any suitable shape including, for example, circular, elliptical, square, rectangular, or any other regular or irregular shape. In an exemplary embodiment, the opening 312 includes an elongated shape having curvilinear sides 314 and end portions 316 defined by a radius. As illustrated in FIG. 3B, the radii at opposite ends 316 of the opening 312 are different. In an alternate embodiment, the radii at opposite ends 316 of the opening 312 are the same. The center points of each of the radii may share a centerline and be centered between the elongated sides 314 of the opening 312.

The opening 312 can include an edge 318 located at the proximal end 308 of the sleeve 300. The edge 318 can include a surface that joins the outer and inner surfaces of the body 302. The edge 318 can be rounded, chamfered, square, or include any other edge formation known in the art. In an exemplary embodiment, the opening 312 can include an edge 318 at various locations around the perimeter of the opening 312. As illustrated in FIG. 3B, in an exemplary embodiment the sleeve can include an edge 318 at the proximal 308 and distal 310 ends of the opening 312. When multiple edges 318 are included, the various edges 318 can include the same or different profile (rounded, chamfered, square, etc.). In an alternate embodiment, the edge 318 can surround the entire perimeter of the opening 312 and have the same or varying profiles at different points around the perimeter of the opening 312.

As illustrated in FIGS. 3A-B, the outer surface of the sleeve body 302 can include a plurality of notches or grooves 320. The grooves 320 can be sized and configured to provide a grip feature for a user. In an exemplary embodiment, the grooves 320 extend in the direction of the longitudinal axis 306 of the sleeve 300 and are substantially parallel to one another around the outside surface of the body 302. In an alternate embodiment (not shown), the grooves 320 can be oriented in a direction other than parallel to the longitudinal axis 306 of the sleeve 300. In a further embodiment (not shown), the grooves can interconnect. As illustrated in FIGS. 3A-B, a groove 320 can include a uniform semi-circular shaped cross-section. In an alternate embodiment, the groove 320 can include a uniform or non-uniform shaped cross-section. In a further embodiment, the groove 320 can include an elliptical, square, rectangular, or any other regular or irregular shaped cross-section.

FIGS. 3C-D provide alternate cross-section view of an exemplary sleeve 300. FIG. 3C shows a top cross-section view an exemplary sleeve 300. In an exemplary embodiment, the central bore 304 of the sleeve 300 may include a mating feature sized and configured for engaging a corresponding mating feature on the knob 500. As illustrated in FIG. 3C, the mating feature may include a raised surface, such as lip 324. Lip 324 can include a raised protrusion extending from the inner body surface 322 toward the longitudinal axis 306 of the sleeve 300. The lip 324 can be sized and located such that it mates with a corresponding recess 520 in the knob body 504. The lip 324 can extend around the entire circumference of the inner body surface 322 or around a portion of the circumference of the inner body surface 322. In an exemplary embodiment, the inner body surface 322 includes a single lip 324. In an alternate exemplary embodiment, inner body surface 322 includes multiple protrusions (lips 324) sized and configured to mate with multiple corresponding recesses 520 in the knob body 504. In an alternate embodiment (not shown), the mating feature may include a recessed portion in the inner body surface 322 sized and configured to mate with a corresponding protrusion on the knob 500. Alternate forms and structures for mechanically mating the sleeve 300 with the knob 500 are contemplated including, for example, threads, press fit, taper fit, bonding fit with the use of adhesive, expansion fit, and mechanical interlocking fit such as a bayonet connection.

As illustrated in FIGS. 3C-D, the central bore 304 can include sections having varying dimension/diameter. In an exemplary embodiment, the portion of the central bore 304 at the proximal end 308 can be sized and configured to accommodate the knob 500. Likewise, in an exemplary embodiment, a portion of the central bore 304 at the distal end 310 can be sized and configured to accommodate the anchor coupling member 400.

In an exemplary embodiment, the distal end 310 of the sleeve 300 can include bore section 326 that is sized and configured to surround the anchor head 102 and locking cap 106. The bore section 326 can extend along the longitudinal axis 306 a distance such that a portion of the length of the anchor head 102 and locking cap 106, when assembled, are surrounded by the bore section 326. In an alternate embodiment, the bore section 326 can extend along the longitudinal axis 306 such that the entire length of the anchor head 102 and locking cap 106 are surrounded by the bore section 326.

In an exemplary embodiment, the distal end 310 of the sleeve 300 includes a saddle portion 328 that abuts the spinal rod 110 or other device restrained between the anchor head 102 and the locking cap 106. In an exemplary embodiment, the saddle portion 328 can include an end sized and shaped to correspond to the profile of the spinal rod 110. The saddle portion 328 may be used to provide a force on the spinal rod 110 in the direction of the longitudinal axis 306. As the saddle portion 328 engages the spinal rod 110 the sleeve 300 and the anchor coupling member 400 work together to splay the threads of the anchor head 102 from the threads of the locking cap 106. In an example sleeve 300, the width of the saddle portion 328 can be sized and configured to correspond to the amount the locking cap 106 and the anchor head 102 splay.

FIGS. 4A-E provide multiple views of the anchor coupling member 400 according to exemplary embodiments of the present disclosure. The anchor coupling member 400 may include a generally cylindrical body 402 with a central bore 404 (see FIG. 4C) extending along the longitudinal axis 406 of the anchor coupling member 400. In an exemplary embodiment, the proximal end 408 of the anchor coupling member 400 is configured to releasably mate with the knob 500. The proximal end 408 of the body 402 can include a mating feature sized and configured to releasably engage a corresponding mating feature of the knob 500. For example, the body 402 if the anchor coupling member 400 can include threads 412 for mating with corresponding threads 512 on the knob 500. Alternate forms and structures for mechanically mating the anchor coupling member 400 with the knob 500 are contemplated including, for example, tongue and groove, press fit, taper fit, bonding fit with the use of adhesive, expansion fit, and mechanical interlocking fit such as a bayonet connection.

As illustrated in FIGS. 4A-E, an exemplary anchor coupling member 400 can include arms 414 extending from the body 402 in the direction of the longitudinal axis 406. In an alternate embodiment (not shown), the anchor coupling member 400 can include a single arm or any number of arms 414 extending from the body 402. The distal end 410 of arms 414 can be sized and configured to surround the anchor head 102 and locking cap 106.

The length of the arms 414 can extend along the longitudinal axis 406 a distance such that only a portion of the length of the anchor head 102 and locking cap 106 are covered by the arms 414. In an alternate embodiment, the length of the arms 414 can extend along the longitudinal axis 406 a distance such that the entire length of the anchor head 102 and locking cap 106 are covered by the arms 414. The width of the central bore 404 at the distal end 410 of the arms 414 can be configured such that the lateral distance between opposing arms 414 is wider than the diameter of the anchor head 102. In an alternate embodiment, the width of the central bore 404 at the distal end 410 of the arms 414 can be configured such that the lateral distance between opposing arms 414 is equal to or less than the width of the anchor head 102. In this embodiment, the arms 414 flex or expand in the lateral direction to accommodate placement of the anchor head 102 between opposing arms 414.

In an exemplary embodiment, the distal end 410 of the arms 414 can include a coupling feature 416 sized and configured to engage a corresponding coupling feature of the bone anchor head 102. The coupling feature 416 can include a slot 418 sized and configured to engage a corresponding protrusion on the outer surface of the bone anchor head 102. In an alternate embodiment (not shown), the coupling feature 416 includes a recessed portion on the inner surface 420 of the arms 416 that mates with a corresponding protrusion on the outer surface of the anchor head 102. In an alternate embodiment (not shown), the coupling feature 416 includes a protrusion from the inner surface 420 of the arms 416 that mates with a corresponding recess on the outer surface of the anchor head 102.

When the release mechanism 200 is assembled, the top wall 422 of the slot 418 engages a protrusion on the bone anchor head 102 and provides a downward force on the top surface of the protrusion. Similarly, the bottom wall 424 of slot 418 engages the protrusion of the bone anchor head 102 and provides an upward force on the bottom surface of the protrusion.

In an exemplary embodiment, the slot 418 can also include a protrusion (or recess (not shown)) for engaging a corresponding recess (or protrusion) in the bone anchor head 102. For example, as illustrated in FIGS. 4A, B and D, the bottom wall 424 of the slot 418 includes a spur 426 for mating with a corresponding recess on the bone anchor head 102.

In an exemplary embodiment, the distal end 410 of the arms 414 include a bottom edge 428 that is sized and configured to engage a corresponding recessed portion on the outer surface of the bone anchor head 102. The bottom edge 428 can include an end surface 430 that engages the recessed portion of the bone anchor head and provides a downward force on the recess surface.

In an exemplary embodiment, the arms 414 of the anchor coupling member 400 include a longitudinal slots 432 extending along the body of the arms 414 in the direction of the longitudinal axis 406. The arms 414 can include a single longitudinal slot 432 or any number of longitudinal slots 432. The size and shape of longitudinal slots 432 can vary. The longitudinal slots 432 can be sized and located to provide flexibility to the arms 414. The longitudinal slots 432 can also provide visibility and access to the central bore 404 and/or any device or tool within the central bore 404. The longitudinal slots 432 can be sized and located to reduce the weight and production material of the anchor coupling member 400. Opposing arms 414 can include matching longitudinal slots 432 or varying numbers, shapes, sizes, and locations of longitudinal slots 432. As illustrated in FIG. 4B, the arms 414 can include longitudinal slots 432a, 432b and 432c. Longitudinal slots 432a, 432b and 432c can each have a different length in the longitudinal direction, slot 432a having the shortest length and slot 432c having the longest length. It is contemplated that the longitudinal slots 432a, 432b and 432c can share a common centerline. In an alternate embodiment (not shown), longitudinal slots 432a, 432b and 432c can each have separate and distinct centerlines with respect to the arm 414.

As illustrated in FIGS. 4A-C, the outer surface of the exemplary anchor coupling member 400 can define a profile that tapers from the proximal end 408 to the distal end 410 of the anchor coupling member 400. In an alternate embodiment (not shown), the outer surface the anchor coupling member 400 defines a profile that maintains a constant dimension along the longitudinal axis 406. In an alternate embodiment (not shown), the outer surface of the anchor coupling member 400 defines a profile that tapers from the distal end 410 to the proximal end 408.

Figure 5A:
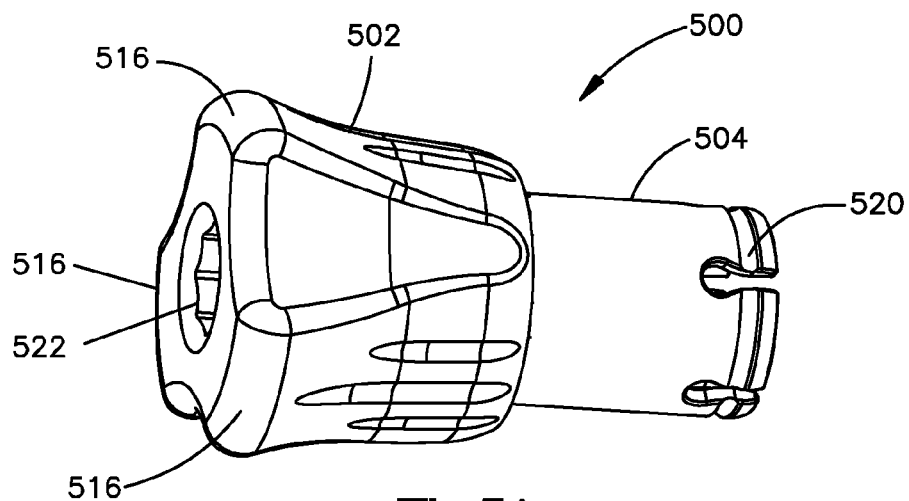
FIG. 5A is a perspective view of an exemplary knob.
Figure 5B:
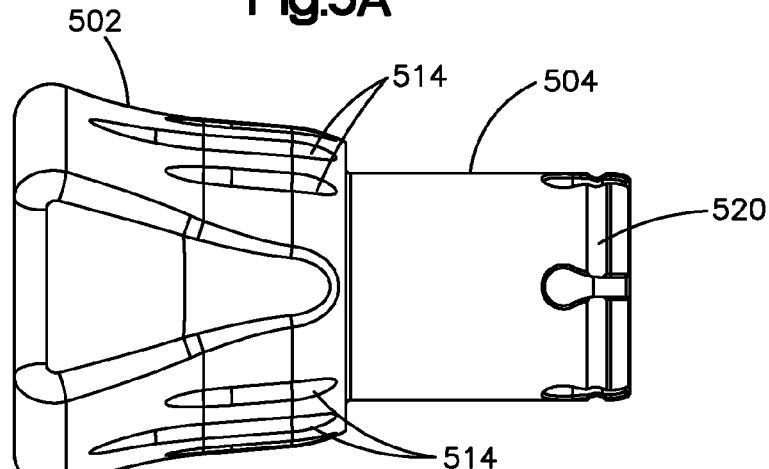
FIG. 5B is a top view of an exemplary knob.
Figure 5C:
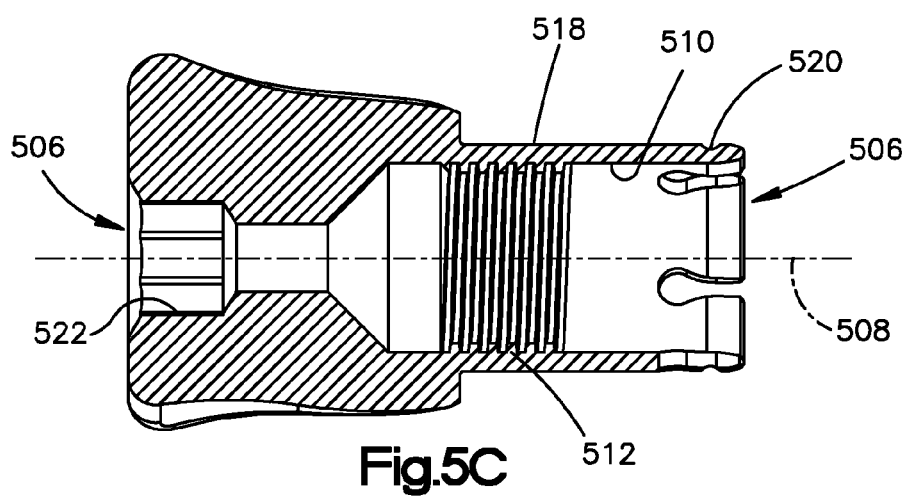
FIG. 5C is a top cross-section view of an exemplary knob.

FIGS. 5A-C provide multiple views of a knob 500 according to exemplary embodiments of the present disclosure. In an exemplary embodiment, the knob 500 includes a handle 502 and a body portion 504, with a central bore 506 extending along the longitudinal axis 508 of the knob 500 through the handle 502 and the body 504. The central bore 506 includes a mating portion sized and configured to releaseably mate the knob 500 with the anchor coupling member 400. For example, an inner surface 510 of the central bore 506 include threads 512 for mating with corresponding threads 412 of the anchor coupling member 400. As illustrated in FIG. 5C, the threads 512 can be located on the inner surface 510 at a position corresponding to the body 504. In an alternate embodiment (not shown), the threads 512 can be located on the inner surface 510 at a position corresponding to the handle 502 or at a position corresponding to both the handle 502 and the body 504.

As illustrated in FIGS. 5A-B, the outer surface of handle 502 can include a plurality of notches or grooves 514. The grooves 514 can be sized and configured to provide a grip feature for a user. In an exemplary embodiment, the grooves 514 extend in the direction of the longitudinal axis 508 of the knob 500 and are substantially parallel to one another around the outside surface of the handle 502. In an alternate embodiment (not shown), the grooves 514 can be oriented in a direction other than parallel to the longitudinal axis 508 of the knob 500. The grooves 514 can align with corresponding grooves 320 on the sleeve 300 to provide for consecutive grooves 514 and 320. The groves 514 on the knob 500 can each have different or similar lengths along the outer surface of the handle 502. In an exemplary embodiment, the grooves 514 can include a uniform semi-circular shaped cross-section. In an alternate embodiment, the groove 514 can include a uniform or non-uniform shaped cross-section. In a further embodiment, the groove 514 can include an elliptical, square, rectangular, or any other regular or irregular shaped cross-section.

In an exemplary embodiment, the handle 502 can include lobes 516 extending radially outward from the handle 502. Each of the lobes 516 are sized and shaped to provide a grip feature for a user. The handle 502 can include a single lobe 516 or any number of lobes 516.

In an exemplary embodiment, the outer surface 518 of the knob body 504 may include a mating feature sized and configured for engaging a corresponding mating feature of the sleeve 300. As illustrated in FIGS. 5A-C, the mating feature may include a recessed surface, such as recess 520. Recess 520 can include a channel extending from the outer surface 518 toward the inner surface 510 of the body 504. The recess 520 can be sized and located such that it mates with a corresponding lip 324 on the sleeve 300. The recess 520 can extend around the entire circumference of the body 504 or around a portion of the circumference of the body 504. In an exemplary embodiment, the outer surface 518 of the body 504 includes a single recess 520. In an alternate embodiment, the outer surface 518 includes multiple recesses 520 sized and configured to mate with multiple corresponding lips 324 on the sleeve 300. In an alternate embodiment (not shown), the mating feature may include a protrusion from the outer surface 518 of the body 504 sized and configured to mate with a corresponding recess on the sleeve 300. The knob body 504 can include a plurality of channels extending along the body at the in the direction of the longitudinal axis 508. The channels can provide for flex to the body 504 as the recess 520 engages the corresponding mating feature of the sleeve 300.

In an exemplary embodiment, the knob 500 includes an indication to identify for the user that the knob 500 is or is not fully engaged within the sleeve 300. In an exemplary embodiment, the indication can include a visual marker on the knob body 504. In an alternate embodiment, the indication can include a locking feature on the outer surface of the knob 500 or a locking feature associated with the threads 512.

As illustrated in FIGS. 5A and 5C, the central bore 506 can include a socket 522 for mating with an associated driver. In an exemplary embodiment, the socket 522 can include an octagon-shaped recess. In an alternative embodiment, the socket 522 can include any other types of sockets or recesses keyed to other known drivers or tools.

In an exemplary embodiment, the release mechanism 200 is assembled by inserting the anchor coupling member 400 into the central bore 304 of the sleeve 300. A portion of the distal end 410 of the anchor coupling member 400 extends through the central bore 304 and out the end of the sleeve 300 to engage the bone anchor 100. A (longitudinal) side of the saddle portion 328 may be aligned with the portion of the anchor coupling member 400 extending out of the sleeve 300. For example, as illustrated in FIG. 2B, the distal end 410 of the arms 414 are located between the saddle portions 328 of the sleeve 300. As a result, when assembled, the anchor coupling member 400 has limited rotatability within the sleeve 300.

As illustrated in FIG. 2B, when assembled (and during assembly), the opening 312 in the sleeve 300 provides visibility of the anchor coupling arms 414 as well as any device or tool within the central bore 404 of the anchor coupling member 400. For example, the user can determine the location and orientation of the arms 414 within the sleeve 300. In an exemplary embodiment, the arms 414 are accessible to the user through the opening 312. For example, the user can access the arms 414 within the sleeve 300 to manipulate or clean the arms 414 while the release mechanism 200 is assembled.

The knob 500 can then be attached to the sleeve 300 and anchor coupling member 400. The knob body 405 is inserted into the central bore 304 of the sleeve 300. A mating feature associated with the sleeve 300 engages a corresponding mating feature of the knob 500. In an exemplary embodiment, the sleeve 300 includes a lip 324 extending from the inner body surface 322. The lip 324 engages a corresponding recess 520 located on the outer surface 518 of the knob body 504 as the knob 500 is inserted into the sleeve 300. In an alternate embodiment, as the knob 500 is inserted into the sleeve 300, the knob 500 reaches a position where the recess 520 momentarily engages the lip 324 and then passes beyond the lip 324 to a final stop position. In an exemplary embodiment, the knob 500 can rotate around its longitudinal axis 508 within the sleeve 300. In an alternate embodiment, rotation of the knob 500 is limited when inserted within the sleeve 300.

In an exemplary embodiment, the knob 500 is attached to the anchor coupling member 400 located within the sleeve 300. In an alternate embodiment, the knob 500 is attached to the anchor coupling member 400 before the anchor coupling member 400 is inserted into the sleeve 300. The knob body 504 is applied to the anchor coupling body 402 and the two pieces are matingly engaged at their corresponding threads 512 and 412. In an exemplary embodiment, as the knob 500 and/or the sleeve 300 is rotated, the threads 512 and 412 threadingly engage until the end of the knob body 504 engages or otherwise contacts the inner body surface 322 of the sleeve 300. In an alternate embodiment, the threads 512 and 412 threadingly engage until the knob handle 502 engages or otherwise contacts the proximal end 308 of the sleeve 300.

The release mechanism 200 is joined to the anchor 100 at the anchor head 102. In an exemplary embodiment, the arms 414 of the anchor coupling member 400 are urged over the bone anchor head such that the coupling feature 416 of the arms 414 mate with a corresponding coupling feature on the bone anchor head 102 and the saddle portion 328 of the sleeve 300 engages a surface of the spinal rod 110. Accordingly, the release mechanism 200 may be engaged with the anchor head 102 of the anchor 100 in situ. The saddle portion 328 provides a contact pressure or a force against the spinal rod 110 and the coupling feature 416 engages the bone anchor head 102 thereby causing the threads of the anchor head 102 and the threads of the locking cap 106 to splay, resulting in the locking cap 106 releasing from the anchor head 102.

A driver or other tool can be inserted through the knob central bore 506 and the anchor coupling central bore 404 to access the locking cap 106. In an exemplary embodiment, the release mechanism 200 to splays the anchor head 102 from the locking cap 106 and a driver engages the locking cap 106 to unthread the locking cap 106 from the anchor head 102. With the locking cap 106 removed from the anchor head 102, the spinal rod 110 can be removed or manipulated.

The release mechanism 200 including the sleeve 300, anchor coupling member 400, and knob 500, and the bone anchor 100 may be made from any biocompatible material known including, for example, metals such as titanium, titanium alloys, stainless steel and cobalt chromium. Other materials include, for example, composites, polymers, ceramics, and any other materials suitable for the release mechanism 200, the anchor 100, and the spinal rod 110. In an exemplary embodiment, the components of the release mechanism 200 include a diamond-like carbon (DLC) coating to reduce friction between the anchor 100 and the release mechanism 200. In a particular embodiment, the sleeve 300 includes a DLC coating. The DLC coating may also prevent destabilization of the passivated layer of steel contacting the anchor 100. In an exemplary embodiment, the components of the release mechanism 200 comprise 17-4PH (precipitation hardened) stainless steel. In a particular embodiment, the anchor coupling member 400 is made of 17-4PH stainless steel. In an exemplary embodiment, the components of the release mechanism 200 comprise "life science" grade PEEK (Ketron 450G PEEK). Life science grade PEEK can improve wear and abrasion characteristics as well as provide high yield strength. In a particular embodiment, the knob 500 is comprised of life science grade PEEK. This prevents metal-to-metal damage between the threads 512 of the knob 500 and the threads 412 of the anchor coupling member 400. Moreover, life science grade PEEK can also reduce the torque required to advance the threads 512 of the knob 500 onto the threads 412 of the anchor coupling member 400.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the following claims.

What is claimed is:

1. A release mechanism for releasing a locking cap threadingly engaged with a bone anchor head, the release mechanism including:
 a sleeve comprising:
  a sleeve bore extending along a longitudinal axis of the sleeve;
  a distal end of the sleeve sized and configured to surround at least a portion of the locking cap and the bone anchor head, the distal end including a saddle portion, the saddle portion configured to abut a rod retained between the locking cap and the bone anchor head;
 an anchor coupling member including:
  a body portion having a proximal end that releasably mates with a knob, the body portion including an inner bore extending along a longitudinal axis of the anchor coupling member;
  at least two arms extending from the body portion, each of the arms sized and configured to cover at least respective portions of the locking cap and the bone anchor head, each of the arms including a coupling feature at a distal end sized and configured to matingly engage a corresponding coupling feature of the bone anchor head;
 the knob including:
  a handle;
  a knob body;
  a knob bore extending through the handle and knob body along a longitudinal axis of the knob, the knob bore including a mating portion for releasably mating the knob with the anchor coupling member;
 wherein the sleeve bore is sized and configured to receive at least a portion of the anchor coupling member and a portion of the knob body.

2. The release mechanism of claim 1, wherein an outer surface of the sleeve includes a curved portion,
 wherein the outer surface of the sleeve includes a tapered portion proximate the distal end of the sleeve.

3. The release mechanism of claim 1, wherein an outer surface of the sleeve includes a cutout, the cutout having an elongated curvilinear shape in a direction along the longitudinal axis of the sleeve.

4. The release mechanism of claim 3, wherein an end portion of the cutout defines a radius.

5. The release mechanism of claim 1, wherein an outer surface of the sleeve includes a groove.

6. The release mechanism of claim 1, wherein the saddle portion is sized and configured to fit between at least one of the arms and the rod,
 wherein a first side and a second side of the saddle portion abuts a side of the at least one arm.

7. The release mechanism of claim 1, wherein the sleeve bore includes a mating feature sized and configured to engage a corresponding mating feature on an outer surface of the knob body.

8. The release mechanism of claim 1, wherein at least a portion of a surface of the sleeve includes a diamond-like carbon (DLC) coating.

9. The release mechanism of claim 1, wherein the coupling feature of each of the arms include a slot sized and configured to engage a protrusion from an outer surface of the bone anchor.

10. The release mechanism of claim 9, wherein the coupling feature of each of the arms further include a bottom edge sized and configured to engage a recessed portion in the outer surface of the bone anchor head.

11. The release mechanism of claim 1, wherein at least one of the arms of the anchor coupling member includes a slot extending in a direction along the longitudinal axis of the anchor coupling member.

12. The release mechanism of claim 1, wherein at least one of the arms of the anchor coupling member includes at least two slots in a direction along the longitudinal axis of the anchor coupling member;
 wherein the length of each of the at least two slots is different.

13. The release mechanism of claim 1, wherein the body portion of the anchor coupling member defines a circumferential perimeter greater than a circumferential perimeter defined by the arms such that a profile of the anchor coupling member tapers in the direction along the longitudinal axis of anchor coupling member.

14. The release mechanism of claim 1, wherein the mating portion of the knob bore includes threads for releasably mating the knob with the anchor coupling member.

15. The release mechanism of claim 1, wherein the handle of the knob includes a lobe portion.

16. The release mechanism of claim 1, wherein the knob body includes a user indication to determine when the knob is not fully engaged within the sleeve.

17. A method of releasing a locking cap attached to a bone anchor, the method comprising:
 assembling a release mechanism including:
  inserting a portion of an anchor coupling member into a bore in a release sleeve;
  aligning a side of a sleeve saddle portion with a side of a coupling feature of the anchor coupling member, where the sleeve saddle portion extends from a distal end of the release sleeve and the coupling feature extends from a distal end of the anchor coupling member;
  attaching a knob to the anchor coupling member by inserting a portion of the knob into the release sleeve such that an inner bore of the knob matingly engages with the anchor coupling member;
 attaching the coupling feature to a corresponding coupling feature on the bone anchor such that the sleeve saddle portion impacts a rod retained between the locking cap and the bone anchor and the coupling feature splays a side of the bone anchor from the locking cap.

18. The method of claim 17, further comprising:
 inserting a driver into a center bore of the release member to mate with a drive feature of the locking cap;
 applying a rotational force to the driver to release a threaded engagement of the locking cap from the bone anchor.

19. The method of claim 17, wherein attaching the coupling feature to the corresponding coupling feature on the bone anchor further comprises:
 expanding the coupling feature over a head and side portion of the bone anchor to engage a recessed channel on the bone anchor.

20. The method of claim 17, wherein attaching the knob to the anchor coupling member further comprises:
 inserting the portion of the knob into the release sleeve such that a mating feature on an outer surface of the portion of the knob releasably mates with a corresponding mating feature located in the bore of the release sleeve.

* * * * *